US009803176B2

(12) United States Patent
Patel

(10) Patent No.: US 9,803,176 B2
(45) Date of Patent: Oct. 31, 2017

(54) METHODS AND COMPOSITIONS FOR THE CLINICAL DERIVATION OF AN ALLOGENIC CELL AND THERAPEUTIC USES

(71) Applicant: Amit Patel, Salt Lake City, UT (US)

(72) Inventor: Amit Patel, Salt Lake City, UT (US)

( * ) Notice: Subject to any disclaimer, the term of this patent is extended or adjusted under 35 U.S.C. 154(b) by 0 days.

(21) Appl. No.: 13/732,204

(22) Filed: Dec. 31, 2012

(65) Prior Publication Data
US 2013/0216505 A1 Aug. 22, 2013

Related U.S. Application Data

(60) Provisional application No. 61/582,070, filed on Dec. 30, 2011, provisional application No. 61/591,211, filed on Jan. 26, 2012.

(51) Int. Cl.
| | |
|---|---|
| C12N 5/073 | (2010.01) |
| C12N 5/071 | (2010.01) |
| C12N 5/0775 | (2010.01) |
| A61K 35/51 | (2015.01) |
| C12N 5/077 | (2010.01) |

(52) U.S. Cl.
CPC ............ *C12N 5/0682* (2013.01); *A61K 35/51* (2013.01); *C12N 5/0605* (2013.01); *C12N 5/0653* (2013.01); *C12N 5/0654* (2013.01); *C12N 5/0655* (2013.01); *C12N 5/0657* (2013.01); *C12N 5/0665* (2013.01)

(58) Field of Classification Search
CPC ................................................... C12N 5/0605
USPC ......................................................... 435/325
See application file for complete search history.

(56) References Cited

U.S. PATENT DOCUMENTS

| | | | |
|---|---|---|---|
| 5,486,359 | A | 1/1996 | Caplan et al. |
| 6,387,367 | B1 | 5/2002 | Davis-Sproul et al. |
| 7,510,873 | B2 | 3/2009 | Mistry et al. |
| 7,547,546 | B2 | 6/2009 | Davies et al. |
| 2003/0161818 | A1 | 8/2003 | Weiss et al. |
| 2010/0216237 | A1 | 8/2010 | Ganchas Soares et al. |
| 2011/0312091 | A1 | 12/2011 | Zhao et al. |

FOREIGN PATENT DOCUMENTS

| | | |
|---|---|---|
| CN | 101890050 | 11/2010 |
| EP | 2540819 | 6/2011 |
| KR | 102009-010957 | 10/2009 |
| WO | WO 2006/019357 A1 | 2/2006 |
| WO | WO 2011/038133 A2 | 3/2011 |

OTHER PUBLICATIONS

Covas et al., Isolation and culture of umbilical vein mesenchymal stem cells. Brazilian Journal of Medical and Biological Research. vol. 36, No. 9 (2003) pp. 1179-1183.*
Panepucci et al., Comparison of gene expression of umbilical cord vein and bone marrow-derived mesenchymal stem cells. Stem Cells. vol. 22 (2004) pp. 1263-1278.*
Kadivar et al., In vitro cardiomyogenic potential of human umbilical vein-derived mesenchymal stem cells. Biochemical and Biophysical Research Communications. vol. 340 (2006) pp. 639-647.*
Secco et al., Mulitpotent stem cells from umbilical cord: cord is richer than blood!. Stem Cells. vol. 26 (2008) pp. 146-150.*
Conconi et al., Phenotype and differentiation potential of stromal populations obtained from various zones of human umbilical cord: an overview. The Open Tissue Engineering and Regenerative Medicine Journal. vol. 4 (2011) pp. 6-20.*
Park et al., Functional expression of ion channels in mesenchymal stem cells derived from umbilical cord vein. Stem Cells. vol. 25, No. 8 (2007) pp. 2044-2052.*
Koh et al., Implantation of human umbilical cord-derived mesenchymal stem cells as a neuroprotective therapy for ischemic stroke in rats. Brain Research. vol. 1229 (2008) pp. 233-248.*
Freshney, R. Ian, Culture of Animal Cells: A Manual of Basic Technique and Specialized Applications, 6th ed. Hoboken, NJ, John Wiley & Sons, Inc., 2011. Chp 2 & 16, pp. 11-23, 269-278. QH585.2.F74 2010.*
Cao, Fu-Jiang, et al.; "Human umbilical cord mesenchymal stem cells and the treatment of spinal cord injury"; Chinese Medical Journal, Jan. 2009; vol. 122, No. 2, pp. 225-231; see abstract; pp. 226-229.
Qiao, Chun, et al.; "Human mesenchymal stem cells isolated from the umbilical cord"; Cell Biology International 32 (2008) vol. 32, No. 1, pp. 8-15; see abstract: pp. 9 & 10.
Capelli et al, "Minimally Manipulated Whole Human Umbilical Cord is a Rich Source of Clinical-Grade Human Mesenchymal Stromal Cells Expanded in Human Platelet Lysate", Cytotherapy, 2011, vol. 13, pp. 786-801, Informa Healthcare.
Deuse et al, "Immunogenicity and Immunomodulatory Properties of Umbilical Cord Lining Mesenchymal Stem Cells", Cell Transplantation, 2011, pp. 655-667, vol. 20, Cognizant Comm. Corp.
Jeschke et al, "Umbilical Cord Lining Membran and Wharton's Jelly-Derived Mesenchymal Stem Cells: The Similarities and Differences" The Open Tissue Engineering and Regenerative Medicine Journal, 2011, vol. 4, pp. 21-27, XP-002696906.
Kita et al, "Isolation and Characterization of Mesenchumal Stem Cells From the Sub-Amniotic Human Umbilical Cord Lining Membrane", Stem Cells and Development, XP-002696905, Nov. 4, 2010, pp. 11, vol. 19, No. 4, Mary Ann Liebert Inc.

(Continued)

*Primary Examiner* — Kara Johnson
(74) *Attorney, Agent, or Firm* — Thorpe North and Western, LLP; Todd B. Alder

(57) ABSTRACT

Various cells, stem cells, and stem cell components, including associated methods of generating and using such cells are provided. In one aspect, for example, an isolated cell that is capable of self-renewal and culture expansion and is obtained from a subepithelial layer of a mammalian umbilical cord tissue. Such an isolated cell expresses at least three cell markers selected from CD29, CD73, CD90, CD166, SSEA4, CD9, CD44, CD146, or CD105, and does not express at least three cell markers selected from CD45, CD34, CD14, CD79, CD106, CD86, CD80, CD19, CD117, Stro-1, or HLA-DR.

15 Claims, 14 Drawing Sheets

(56) References Cited

OTHER PUBLICATIONS

Lai et al, "Mesenchymal Stem Cell Exosome: A Novel Stem Cell-Based Therapy for Cardiovascular Disease", Regen Med, 2011, vol. 6, No. 4, pp. 481-492, ISSN 1746-0751.

Patel e al, "Mesenchymal stem Cell Population Isolated From the Subepithelial Layer of Umbilical Cord Tissue", Cell Transplantation, 2013, vol. 22, pp. 513-519, Cognizant Comm. Corp.

Search Report for European application 12862921.9 dated Apr. 22, 2015, 13 pages.

\* cited by examiner

METHODS AND COMPOSITIONS FOR THE CLINICAL DERIVATION OF AN ALLOGENIC CELL AND THERAPEUTIC USES

PRIORITY DATA

This application claims the benefit of U.S. Provisional Patent Application Ser. No. 61/582,070, filed on Dec. 30, 2011, and of U.S. Provisional Patent Application Ser. No. 61/591,211, filed on Jan. 26, 2012, both of which are incorporated herein by reference in their entireties.

FIELD OF THE INVENTION

The present invention relates generally to stem cells and various related aspects thereof. Accordingly, the present invention involves the fields of chemistry, life science, and medicine.

BACKGROUND

Various cell and stem cell populations have been shown to have value for research applications. However, clinical translation of these cell types for human and animal use in therapeutic applications is limited due to a number of reasons, including allogenic issues.

SUMMARY

The present disclosure provides various cells, stem cells, and stem cell components, including associated methods of generating and using such cells. In one aspect, for example, an isolated cell that is capable of self-renewal and culture expansion and is obtained from a subepithelial layer of a mammalian umbilical cord tissue is provided. Such an isolated cell expresses at least three cell markers selected from CD29, CD73, CD90, CD166, SSEA4, CD9, CD44, CD146, or CD105, and does not express at least three cell markers selected from CD45, CD34, CD14, CD79, CD106, CD86, CD80, CD19, CD117, Stro-1, or HLA-DR. In another aspect, the isolated cell expresses CD29, CD73, CD90, CD166, SSEA4, CD9, CD44, CD146, and CD105. In yet another aspect, the isolated cell does not express CD45, CD34, CD14, CD79, CD106, CD86, CD80, CD19, CD117, Stro-1, and HLA-DR. In some aspects, the isolated cell can be positive for SOX2, OCT4, or both SOX2 and OCT4. In a further aspect, the isolated cell can produce exosomes expressing CD63, CD9 or both. It is understood that the present scope includes cultures of isolated cells.

The cells according to aspects of the present disclosure are capable of differentiation into a variety of cell types, and any such cell type is considered to be within the present scope. Non-limiting examples of such cell types can include adipocytes, chondrocytes, osteocytes, cardiomyocytes, endothelial cells, myocytes, and the like, including combinations thereof.

A variety of cells and cellular products can be derived from the isolated cells described herein, and any such cells and cellular products are considered to be within the present scope. In one aspect, for example, the present disclosure provides an isolated exosome derived from the isolated cells described, where the exosome expresses CD63, CD9 or both. In another aspect, an adipocyte cell that has been differentiated from the isolated cells described is provided. In yet another aspect, a chondrocyte cell that has been differentiated from the isolated cells described is provided. In a further aspect, an osteocyte cell that has been differentiated from the isolated cells described is provided. In yet a further aspect, a cardiomyocyte cell that has been differentiated from the isolated cells described is provided. Furthermore, a culture of differentiated cells derived from the isolated cells described including at least one cell type selected from an adipocyte, a chondrocyte, an osteocyte, or a cardiomyocyte is provided.

In another aspect, the present disclosure provides a method of culturing stem cells from a subepithelial layer of a mammalian umbilical cord. Such a method can include dissecting the subepithelial layer from the umbilical cord, placing the dissected subepithelial layer interior side down on a substrate such that an interior side of the subepithelial layer is in contact with the substrate, and culturing the subepithelial layer on the substrate. The method can additionally include removing explants for primary cell expansion. In one aspect, dissecting the subepithelial layer further includes removing Wharton's Jelly from the umbilical cord.

The subepithelial layer can be cultured in any media capable of producing explants therefrom, and any such medium is considered to be within the present scope. In one specific aspect, however, one such culture medium can include a platelet lysate. In another aspect, the culture media can include human or animal platelet lysate. In yet another aspect, the culture media can be derived from human-free and animal-free ingredients.

The substrate utilized to culture the subepithelial layer can be any substrate capable of deriving explants therefrom. In one aspect, the substrate can be a polymeric matrix. One example of such a polymeric matrix is a culture dish. In one specific aspect, the culture dish can be a cell culture treated plastic, and the subepithelial layer can be placed thereon without any additional pretreatment to the cell culture treated plastic. In another aspect, the substrate can be a semi-solid cell culture substrate. Any type of semi-solid substrate that is capable of supporting the subepithelial layer during the culturing procedure is considered to be within the present scope.

Various culturing conditions are contemplated, and it is understood that such conditions can vary depending on experimental protocol and various desired results. In one aspect, for example, the subepithelial layer can be cultured in a normoxic environment. In another aspect, the subepithelial layer can be cultured in a hypoxic environment. Additionally, in some aspects, the culturing of the subepithelial layer and the removal of the explants can be performed without the use of any enzymes. Furthermore, in some aspects, subculturing of the explants and/or the cells resulting from the explants can be performed without the use of any enzymes.

In yet another aspect of the present disclosure, a method of treating a medical condition responsive to treatment with the isolated cells described herein can include introducing such cells into an individual having the medical condition. These cellular treatments can be utilized to treat any condition for which they are capable providing a benefit. Non-limiting examples of such medical conditions include COPD, diabetes, ischemia, osteoarthritis, orthopedic damage, liver damage, chronic refractory angina, erectile dysfunction, herniated disks, congestive heart failure, asthma, emphysema, wounds, acute radiation syndrome, autoimmune disorders, ischemic organ beds, graft vs. host disease, and the like, including combinations thereof. Additionally, in another aspect, a method of treating a medical condition responsive to treatment with the differentiated cells described herein can include introducing at least one cell type of the differentiated cells into an individual having the medical condition.

In a further aspect, a method of treating COPD is provided. Such a method can include administering a COPD effective active agent intravenously to a subject to deliver the COPD effective active agent to a lower half of the subject's lung, and administering the COPD effective active agent in an aerosolized form to the subject via ventilation to deliver the COPD effective active agent to an upper half of the subject's lung. In one aspect, the COPD effective active agent includes stem cells. In yet another aspect, the stem cells include cells derived from the subepithelial layer of a mammalian umbilical cord as has been described herein. In one specific aspect, the stem cells can be aerosolized with an aerosolizer to a size of from about 6 to about 200 microns. Additionally, the two types of administration can be delivered sequentially or concomitantly.

In another aspect, the COPD effective active agent can be an active agent other than stem cells. Non-liming examples of such COPD effective active agents can include exosomes, cell lysates, protein extracts derived from cell culture, and the like, including combinations thereof.

BRIEF DESCRIPTION OF THE DRAWINGS

FIG. 1 shows an image of a histological section of umbilical cord identifying the subepethelial layer in accordance with one aspect of the present disclosure.

FIG. 2A shows explant of cells migrating from the subepithelial layer and karyotyping of cells in accordance with another aspect of the present disclosure.

FIG. 2B shows explant of cells migrating from the subepithelial layer and karyotyping of cells in accordance with another aspect of the present disclosure.

FIG. 2C shows karyotyping of cells in accordance with another aspect of the present disclosure FIG. 3A shows FACS analysis of cell determinant markers expressed by cells or stem cells derived from umbilical cord in accordance with another aspect of the present disclosure.

FIG. 3B shows FACS analysis of cell determinant markers expressed by cells or stem cells derived from umbilical cord in accordance with another aspect of the present disclosure.

FIG. 3C shows FACS analysis of cell determinant markers expressed by cells or stem cells derived from umbilical cord in accordance with another aspect of the present disclosure.

FIG. 3D shows FACS analysis of cell determinant markers expressed by cells or stem cells derived from umbilical cord in accordance with another aspect of the present disclosure.

FIG. 3E shows FACS analysis of cell determinant markers expressed by cells or stem cells derived from umbilical cord in accordance with another aspect of the present disclosure.

FIG. 3F shows FACS analysis of cell determinant markers expressed by cells or stem cells derived from umbilical cord in accordance with another aspect of the present disclosure.

FIG. 3G shows FACS analysis of cell determinant markers expressed by cells or stem cells derived from umbilical cord in accordance with another aspect of the present disclosure.

FIG. 3H shows FACS analysis of cell determinant markers expressed by cells or stem cells derived from umbilical cord in accordance with another aspect of the present disclosure.

FIG. 3I shows FACS analysis of cell determinant markers expressed by cells or stem cells derived from umbilical cord in accordance with another aspect of the present disclosure.

FIG. 3J shows FACS analysis of cell determinant markers expressed by cells or stem cells derived from umbilical cord in accordance with another aspect of the present disclosure.

FIG. 3K shows FACS analysis of cell determinant markers expressed by cells or stem cells derived from umbilical cord in accordance with another aspect of the present disclosure.

FIG. 3L shows FACS analysis of cell determinant markers expressed by cells or stem cells derived from umbilical cord in accordance with another aspect of the present disclosure.

FIG. 3M shows FACS analysis of cell determinant markers expressed by cells or stem cells derived from umbilical cord in accordance with another aspect of the present disclosure.

FIG. 3N shows FACS analysis of cell determinant markers expressed by cells or stem cells derived from umbilical cord in accordance with another aspect of the present disclosure.

FIG. 3O shows FACS analysis of cell determinant markers expressed by cells or stem cells derived from umbilical cord in accordance with another aspect of the present disclosure.

FIG. 4A shows images of RT-PCR analysis of RNA extracted from cells or stem cells derived from umbilical cord in accordance with another aspect of the present disclosure.

FIG. 4B shows images of immunocytochemical staining of cells in accordance with another aspect of the present disclosure.

FIG. 4C shows images of immunocytochemical staining of cells in accordance with another aspect of the present disclosure.

FIG. 4D shows images of immunocytochemical staining of cells in accordance with another aspect of the present disclosure.

FIG. 5A shows images of culture of cells or stem cells derived from umbilical cord tissue in semi-solid PRP matrix or PL Lysate in accordance with another aspect of the present disclosure.

FIG. 5B shows images of culture of cells or stem cells derived from umbilical cord tissue in semi-solid PRP matrix or PL Lysate in accordance with another aspect of the present disclosure.

FIG. 6A shows extracellular exosome size analysis in accordance with another aspect of the present disclosure.

FIG. 6B shows an SEM of exosomes in accordance with another aspect of the present disclosure.

FIG. 6C shows CD63 expression of exosomes produced from cells or stem cells derived from umbilical cord in accordance with another aspect of the present disclosure.

FIG. 6D shows CD63 expression of exosomes produced from cells or stem cells derived from umbilical cord in accordance with another aspect of the present disclosure.

FIG. 7A shows images demonstrating differentiation of umbilical cord tissue into adipogeneic lineages in accordance with another aspect of the present disclosure.

FIG. 7B shows images demonstrating differentiation of umbilical cord tissue into adipogeneic lineages in accordance with another aspect of the present disclosure.

FIG. 7C shows images demonstrating differentiation of umbilical cord tissue into adipogeneic lineages in accordance with another aspect of the present disclosure.

FIG. 7D shows images demonstrating differentiation of umbilical cord tissue into adipogeneic lineages in accordance with another aspect of the present disclosure.

DETAILED DESCRIPTION

Figure 1:
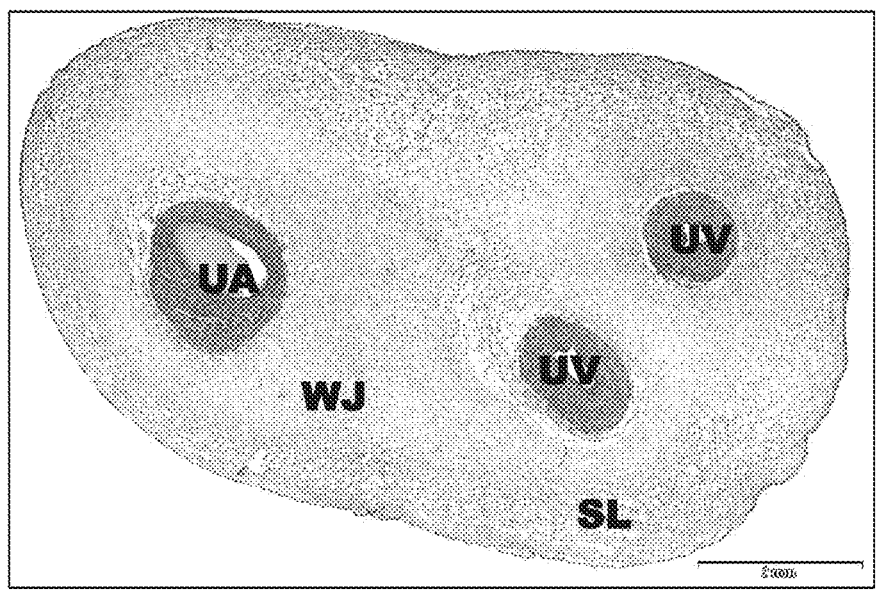

Before the present disclosure is described herein, it is to be understood that this disclosure is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

Definitions

The following terminology will be used in accordance with the definitions set forth below.

It should be noted that, as used in this specification and the appended claims, the singular forms "a," and, "the" include plural referents unless the context clearly dictates otherwise. Thus, for example, reference to "a cell" includes one or more of such cells and reference to "the flask" includes reference to one or more of such flasks.

As used herein, the term "isolated cell" refers to a cell that has been isolated from the subepithelial layer of a mammalian umbilical cord.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

The Disclosure

The present disclosure presents a novel discovery of an allogenic cell or stem cell population that can be used for treating a wide range of conditions. In addition this disclosure describes a novel media and method of culturing these cells without, in some cases, the use of animal products or enzymes. As such, cells, stem cells, cell cultures, and associated methods, including methods of isolating, culturing, developing, or otherwise producing these cells are provided. The scope of the present disclosure additionally encompasses research and therapeutic uses of such cell and cell cultures, including compounds derived therefrom.

As one example, the cell and stem cell populations and compounds derived from these populations may be used in allogenic applications to treat a wide range of conditions including, but not limited to, cardiac, orthopedic, autoimmune, diabetes, cardio vascular disorders, neurological, erectile dysfunction, spinal cord injuries, herniated disks, critical limb ischemia, hypertension, wound healing, ulcers, chronic obstructive lung disease, acute radiation syndrome, graft vs. host disease, ischemic organ beds and the like. Also described are methods of producing cell and stem cell populations and compounds that may be used for drug discovery and development, as well as toxicology testing. Examples of compounds derived from these cell and stem cell populations are small vesicles that contain proteins, RNA, micro RNAs, and the like, that are specific to the cell and stem cell populations.

In one aspect, an isolated cell obtained from a subepithelial layer of a mammalian umbilical cord tissue capable of self-renewal and culture expansion is provided. Such a cell is capable of differentiation into a cell type such as, in one aspect for example, adipocytes, chondrocytes, osteocytes, cardiomyocytes, and the like. In another aspect, non-limiting examples of such cell types can include white, brown, or beige adipocytes, chondrocytes, osteocytes, cardiomyocytes, endothelial cells, myocytes, and the like, including combinations thereof. Other examples of such cell types can include neural progenitor cells, hepatocytes, islet cells, renal progenitor cells, and the like.

A cross section of a human umbilical cord is shown in FIG. 1, which shows the umbilical artery (UA), the umbilical veins (UV), the Wharton's Jelly (WJ), and the subepithelial layer (SL). Isolated cells from the SL can have a variety of characteristic markers that distinguish them from cell previously isolated from umbilical cord samples. It should be noted that these isolated cells are not derived from the Wharton's Jelly, but rather from the SL.

Various cellular markers that are either present or absent can be utilized in the identification of these SL-derived cells, and as such, can be used to show the novelty of the isolated cells. For example, in one aspect, the isolated cell expresses at least three cell markers selected from CD29, CD73, CD90, CD146, CD166, SSEA4, CD9, CD44, CD146, or CD105, and the isolated cell does not express at least three cell markers selected from CD45, CD34, CD14, CD79, CD106, CD86, CD80, CD19, CD117, Stro-1, or HLA-DR. In another aspect, the isolated cell expresses at least five cell markers selected from CD29, CD73, CD90, CD146, CD166, SSEA4, CD9, CD44, CD146, or CD105. In another aspect, the isolated cell expresses at least eight cell markers selected from CD29, CD73, CD90, CD146, CD166, SSEA4, CD9, CD44, CD146, or CD105. In a yet another aspect, the isolated cell expresses at least CD29, CD73, CD90, CD166, SSEA4, CD9, CD44, CD146, and CD105. In another aspect, the isolated cell does not express at least five cell markers selected from CD45, CD34, CD14, CD79, CD106, CD86, CD80, CD19, CD117, Stro-1, or HLA-DR. In another aspect, the isolated cell does not express at least eight cell markers selected from CD45, CD34, CD14, CD79, CD106, CD86, CD80, CD19, CD117, Stro-1, or HLA-DR. In yet another aspect, the isolated cell does not express at least CD45, CD34, CD14, CD79, CD106, CD86, CD80, CD19, CD117, Stro-1, and HLA-DR. Additionally, in some aspects, the isolated cell can be positive for SOX2, OCT4, or both SOX2 and OCT4. In a further aspect, the isolated cell can produce exosomes expressing CD63, CD9, or both CD63 and CD9.

A variety of techniques can be utilized to extract the isolated cells of the present disclosure from the SL, and any such technique that allows such extraction without significant damage to the cells is considered to be within the present scope. In one aspect, for example, a method of culturing stem cells from the SL of a mammalian umbilical cord can include dissecting the subepithelial layer from the umbilical cord. In one aspect, for example, umbilical cord tissue can be collected and washed to remove blood, Wharton's Jelly, and any other material associated with the SL. For example, in one non-limiting aspect the cord tissue can be washed multiple times in a solution of Phosphate-Buffered Saline (PBS) such as Dulbecco's Phosphate-Buffered Saline (DPBS). In some aspects the PBS can include a platelet lysate (i.e. 10% PRP lysate of platelet lysate). Any remaining Wharton's Jelly or gelatinous portion of the umbilical cord can then be removed and discarded. The remaining umbilical cord tissue (the SL) can then be placed interior side down on a substrate such that an interior side of the SL is in contact with the substrate. An entire dissected umbilical cord with the Wharton's Jelly removed can be placed directly onto the substrate, or the dissected umbilical cord can be cut into smaller sections (e.g. 1-3 mm) and these sections can be placed directly onto the substrate.

A variety of substrates are contemplated upon which the SL can be placed. In one aspect, for example, the substrate can be a solid polymeric material. One example of a solid polymeric material can include a cell culture dish. The cell culture dish can be made of a cell culture treated plastic as is known in the art. In one specific aspect, the SL can be placed upon the substrate of the cell culture dish without any additional pretreatment to the cell culture treated plastic. In another aspect, the substrate can be a semi-solid cell culture substrate. Such a substrate can include, for example, a semi-solid culture medium including an agar or other gelatinous base material.

Figure 2A:
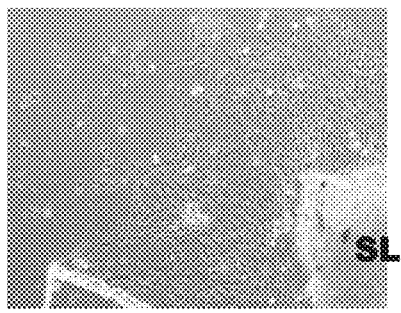
Figure 2B:
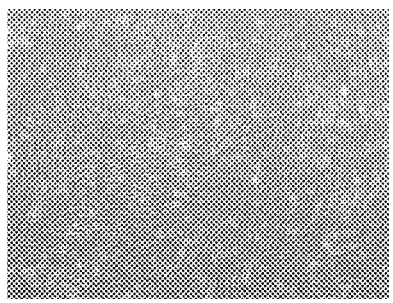
Figure 2C:
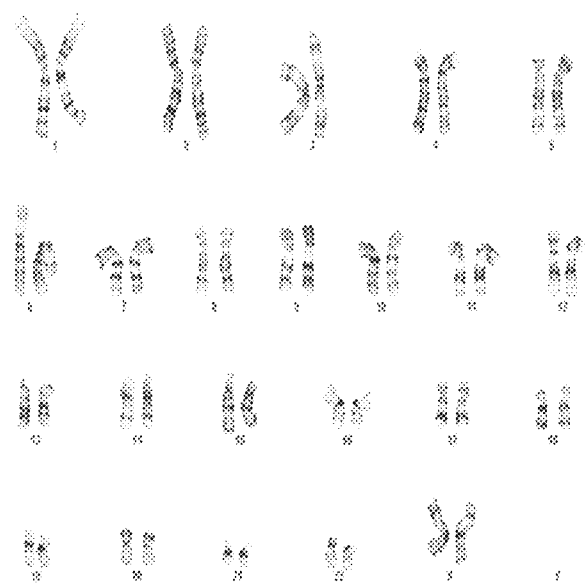
Figure 3A:
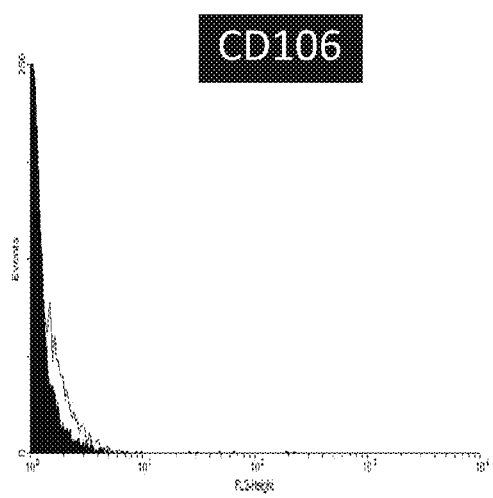
Figure 3B:
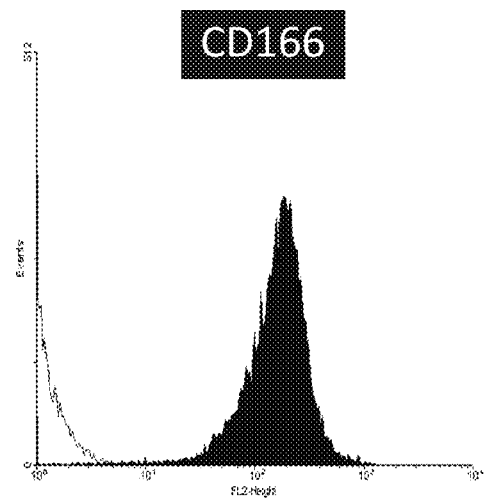
Figure 3C:
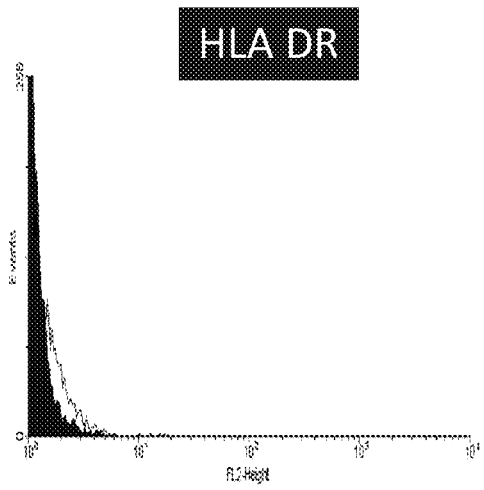
Figure 3D:
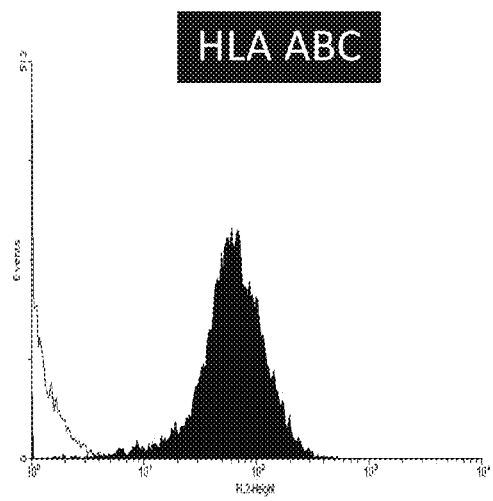
Figure 3E:
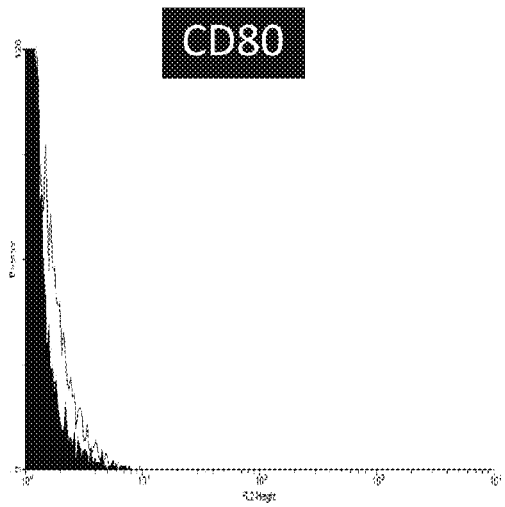
Figure 3F:
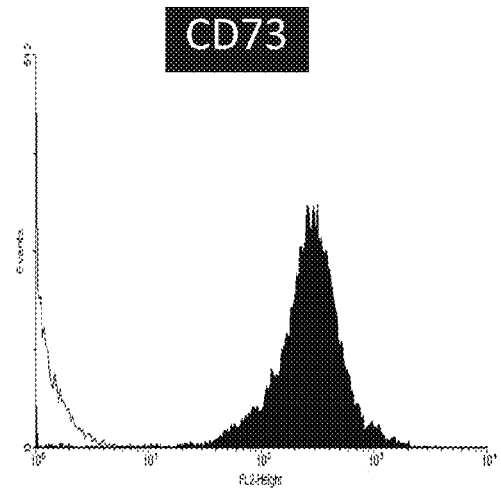
Figure 3G:
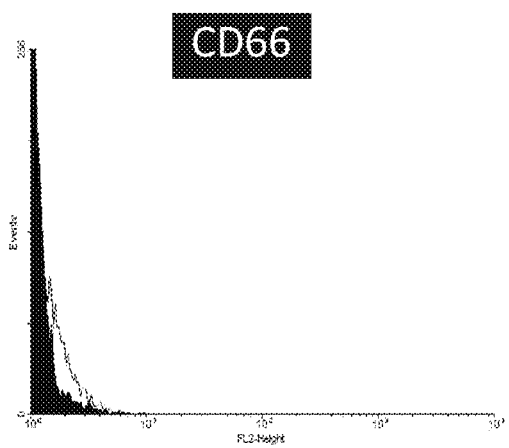
Figure 3H:
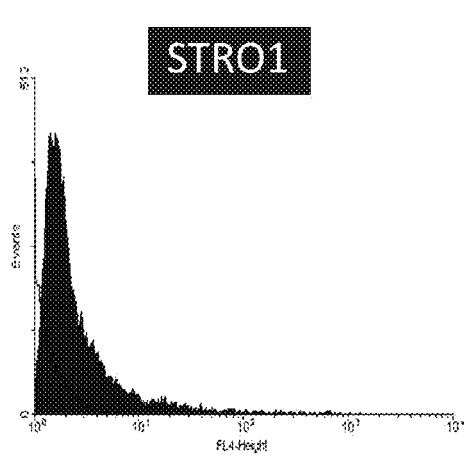
Figure 3I:
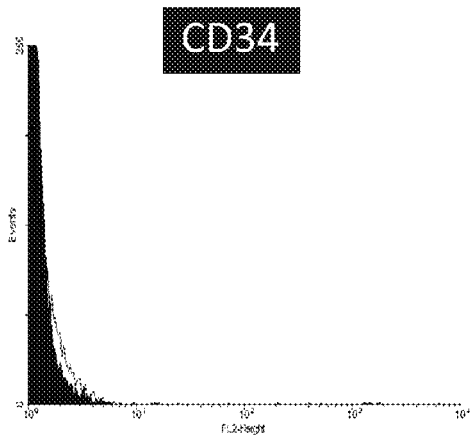
Figure 3J:
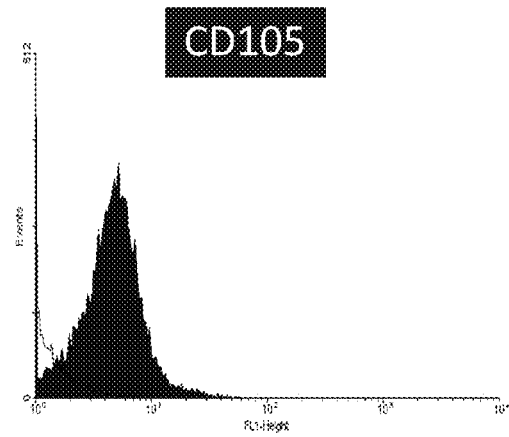
Figure 3K:
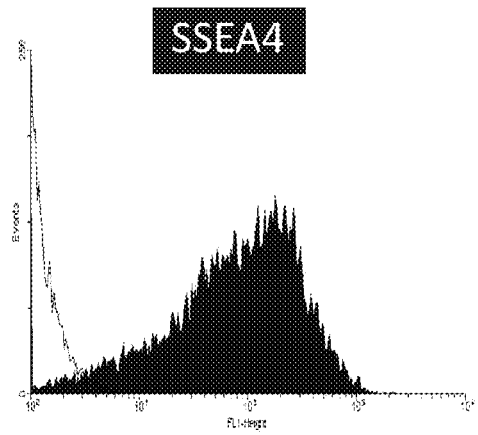
Figure 3L:
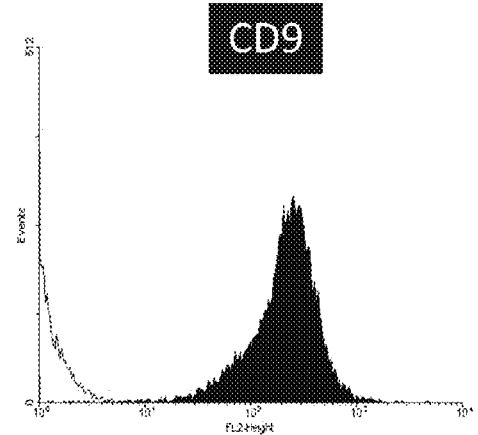
Figure 3M:
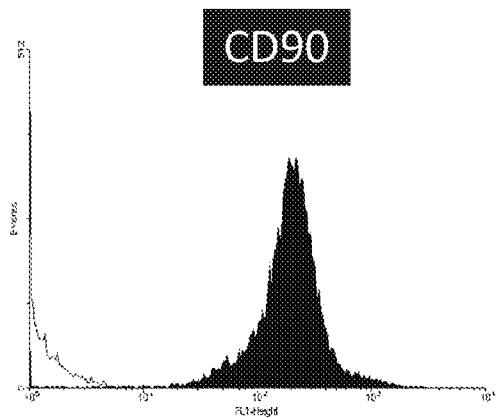
Figure 3N:
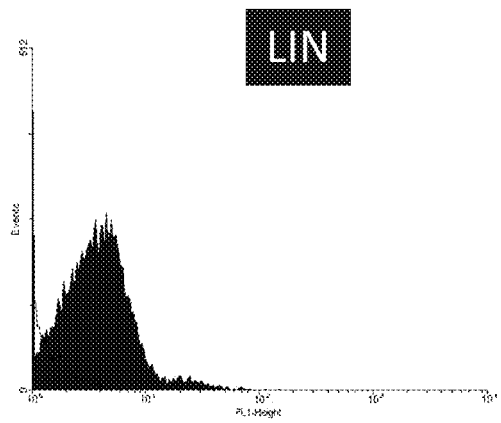
Figure 3O:
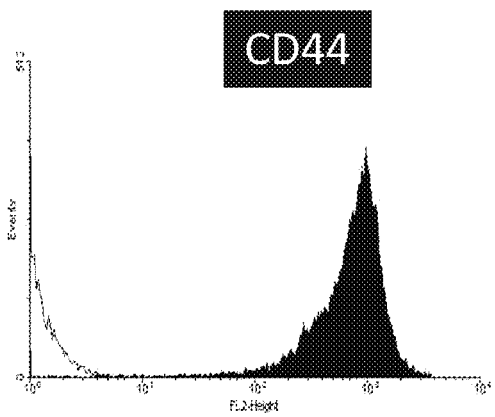
Figure 4A:
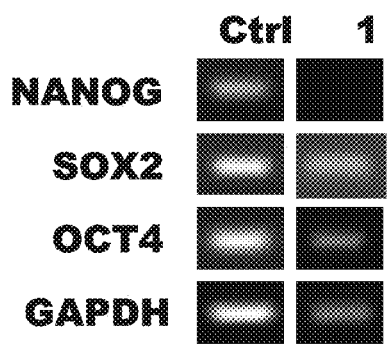
Figure 4B:
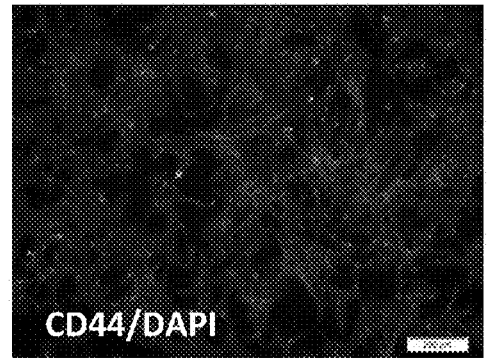
Figure 4C:
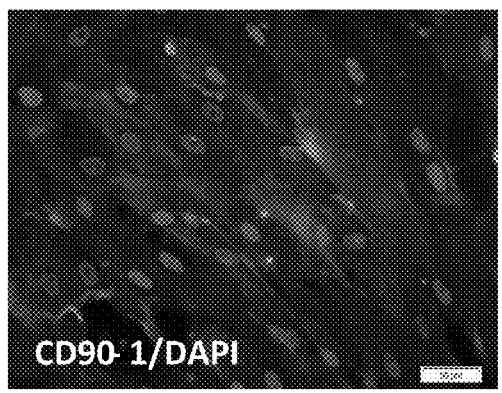
Figure 4D:
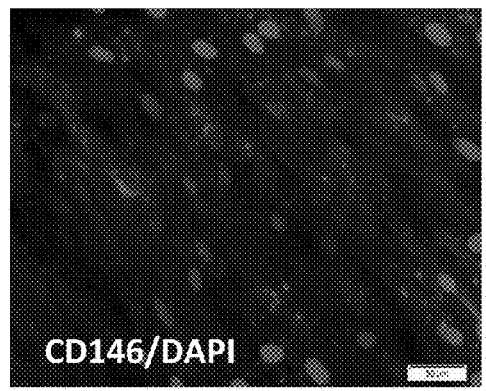

Following placement of the SL on the substrate, the SL is cultured in a suitable medium. In some aspects it is preferable to utilized culture media that is free of animal and human components or contaminants. As one example, FIG. 2 shows the culturing of cells from the SL. As can be seen in FIG. 2A, at three days post plating of the SL, cells have begun to migrate. FIG. 2B shows cells after 6 days of culture in animal free media. Furthermore, FIG. 2C shows the karyotype of cells following passage 12. As has been described, the cells derived from the SL have a unique marker expression profile. Data showing a portion of this profile is shown in FIGS. 3A-O.

The culture can then be cultured under either normoxic or hypoxic culture conditions for a period of time sufficient to establish primary cell cultures. (e.g. 3-7 days in some cases). After primary cell cultures have been established, the SL tissue is removed and discarded. Cells or stem cells are further cultured and expanded in larger culture flasks in either a normoxic or hypoxic culture conditions. While a variety of suitable cell culture media are contemplated, in one non-limiting example the media can be Dulbecco's Modified Eagle Medium (DMEM) glucose (500-6000 mg/mL) without phenol red, 1× glutamine, 1× NEAA, and 0.1-20% PRP lysate or platelet lysate. Another example of suitable media can include a base medium of DMEM low glucose without phenol red, 1× glutamine, 1× NEAA, 1000 units of heparin and 20% PRP lysate or platelet lysate. In another example, cells can be cultured directly onto a semi-solid substrate of DMEM low glucose without phenol red, 1× glutamine, 1× NEAA, and 20% PRP lysate or platelet lysate. In a further example, culture media can include a low glucose medium (500-1000 mg/mL) containing 1× Glutamine, 1× NEAA, 1000 units of heparin. In some aspects, the glucose can be 1000-4000 mg/mL, and in other aspects the glucose can be high glucose at 4000-6000 mg/mL. These media can also include 0.1%-20% PRP lysate or platelet lysate. In yet a further example, the culture medium can be a semi-solid with the substitution of acid-citrate-dextrose ACD in place of heparin, and containing low glucose medium (500-1000 mg/mL), intermediate glucose medium (1000-4000 mg/mL) or high glucose medium (4000-6000 mg/mL), and further containing 1× Glutamine, 1× NEAA, and 0.1%-20% PRP lysate or platelet lysate. In some aspects, the cells can be derived, subcultured, and/or passaged using TrypLE. In another aspect, the cells can be derived, subcultured, and/or passaged without the use of TrypLE or any other enzyme.

FIG. 4 shows data relating to various genetic characteristics of the cells isolated from the SL tissue. FIG. 4A shows that isolated SL cells (lane 1) are positive for SOX2 and OCT4, and are negative for NANOG as compared to control cells (Ctrl). FIG. 4B shows a DAPI stained image of cultured SL cells demonstrating that such cells are positive for CD44. FIG. 4C shows a DAPI stained image of cultured SL cells demonstrating that such cells are positive for CD90. FIG. 4D shows a DAPI stained image of cultured SL cells demonstrating that such cells are positive for CD 146.

Figure 5A:
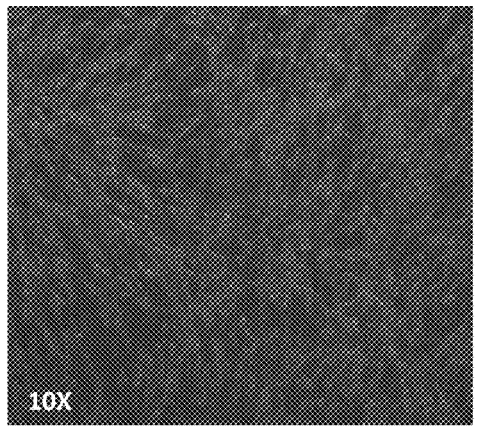
Figure 5B:
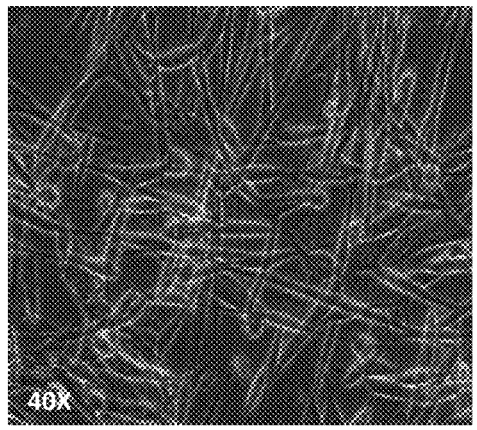

In one aspect, SL cells can be cultured from a mammalian umbilical cord in a semi-solid PRP Lysate or platelet lysate substrate. Such cells can be cultured directly onto a plastic coated tissue culture flask as has been described elsewhere herein. After a sufficient time in either normoxic or hypoxic culture environments the media is changed and freshly made semi-solid PRP lysate or platelet lysate media is added to the culture flask. The flask is continued to be cultured in either a normoxic or hypoxic culture environment. The following day the media becomes a semi-solid PRP-lysate or platelet lysate matrix. The cells can be continued to be cultured in this matrix being until further use. FIGS. 5A and B show SL cells growing in a semi-solid PRPL or PL gel at 10× and 40× magnifications. In one specific aspect, ingredients for a semi solid culture can include growth factors for expanded cell culture of differentiation. Non-limiting examples can include FGF, VEGF, FNDC5, 5-azacytidine, TGF-Beta1, TGF Beta2, insulin, ITS, IGF, and the like, including combinations thereof.

In some cases, allogenic confirmation of SL cells, either differentiated or undifferentiated, can be highly beneficial, particularly for therapeutic uses of the cells. In such cases, mixed lymphocyte reactions can be performed on the cells to confirm the allogenic properties of the cells. In certain aspects, a cell derived as described herein does not cause a mixed lymphocyte response or T-cell proliferation.

In certain aspects, a cell derived as described herein can be recombinantly modified to express one or more genes and or proteins. In one technique, a gene or genes can be incorporated into an expression vector. Approaches to deliver a gene into the cell can include without limitation, viral vectors, including recombinant retroviruses, adenoviruses, adeno-associated virus, lentivirus, poxivirus, alphavirus, herpes simplex virus-1, recombinant bacterial, eukaryotic plasmids, and the like, including combinations thereof. Plasmid DNA may be delivered naked or with the help of exosomes, cationic liposomes or derivatized (antibody conjugated) polylysine conjugates, gramicidin S, artificial viral envelopes, other intracellular carriers, as well as direct injection of the genes. In some aspects, non-viral gene delivery methods can be used, such as for example, scaffold/matrix attached region (S/MAR)-based vector.

Figure 6A:
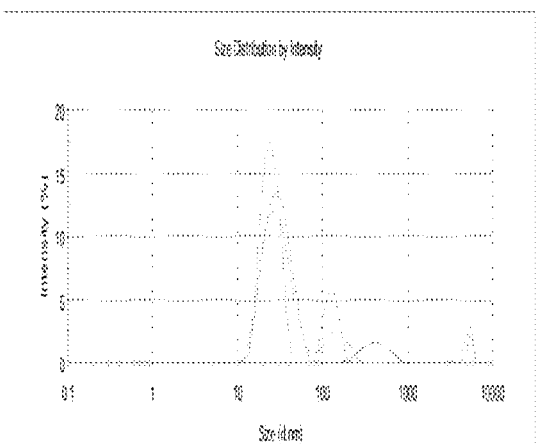
Figure 6B:
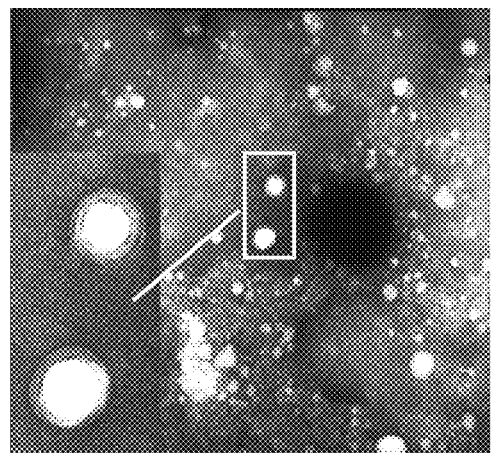
Figure 6C:
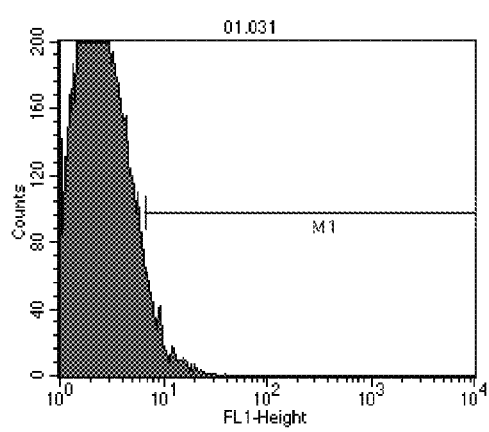
Figure 6D:
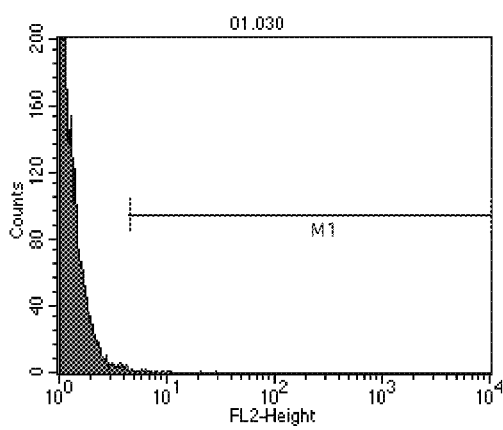

Furthermore, in some aspects, isolated SL cells can be used to produce an exosome population. These exosome populations can be utilized for a variety of research and therapeutic uses. In one aspect, for example, cells are cultured as described in either a normoxic or hypoxic culture environment and supernatants are collected at each media change. Exosomes can then be purified from the supernatants using an appropriate purification protocol. One not-limiting example of such a protocol is the ExoQuick isolation system by SYSTEMBIO. Purified exosomes can be utilized for further manipulation, targeting, and therapeutic use. The exosomes specific to the SL cells are positive for CD63 expression. FIG. 6A shows an analysis of the size of exosomes obtained as has been described, and FIG. 6B shows and electron microscope image of a sampling of exosomes. Additionally, FIGS. 6C-D show CD63 expression of exosomes produced from cells or stem cells derived from umbilical cord.

In some aspects, the isolated cells and cell cultures can be utilized as-is upon isolation from the SL tissue. In other aspects, the isolated cells can be differentiated into other cell types. It should be noted that any useful cell type that can be derived from the cells isolated from SL tissue are considered to be within the present scope. Non-limiting examples of such cell types include adipocytes, chondrocytes, osteocytes, cardiomyocytes, and the like. Differentiation can be induced by exposing the cells to chemicals, growth factors, supernatants, synthetic or naturally occurring compounds, or any other agent capable of transforming the cells. In one aspect, for example, the isolated cells can be differentiated into adipocytes, as is shown in FIG. 7.

Figure 7A:
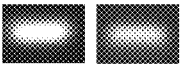

Any technique for differentiation of SL cells into adipocytes is considered to be within the present scope. One non-limiting example used for adipogenic differentiation includes SL cells cultured in the presence of StemPro Adipogenic Differentiation media (Life Technologies). FIG. 7A shows differentiated SL cells that are positive for the adipogenic markers FABP4, LPL, and PPARy (lane 1). For adipogenic differentiation, confirmation was determined by Oil Red O staining and FABP4 immunocytochemistry.

Figure 7B:
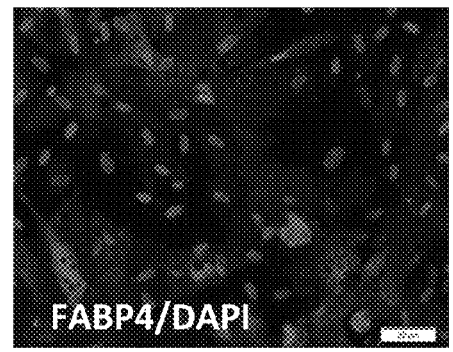
Figure 7C:
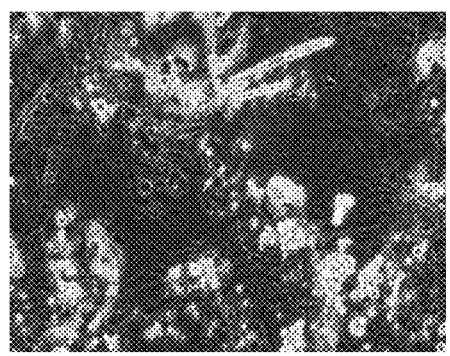
Figure 7D:
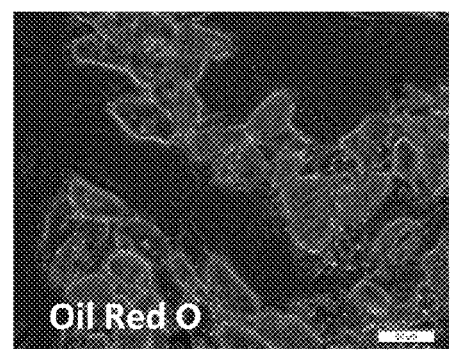

FIG. 7B shows an image of DAPI stained cells showing FABP4 markers. FIG. 7C shows unstained cells and FIG. 7D shows Oil Red O staining demonstrating the storage of fats in the cells.

Figure 8A:
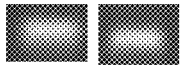
FIG. 8A shows images demonstrating differentiation of umbilical cord tissue into osteogenic lineages in accordance with another aspect of the present disclosure.
Figure 8B:
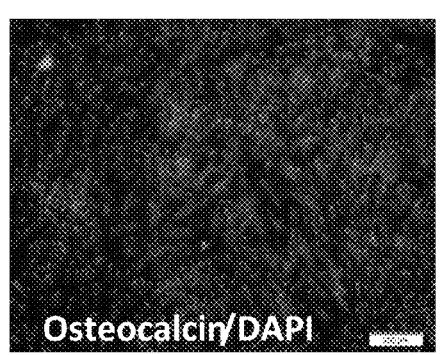
FIG. 8B shows images demonstrating differentiation of umbilical cord tissue into osteogenic lineages in accordance with another aspect of the present disclosure.
Figure 8C:
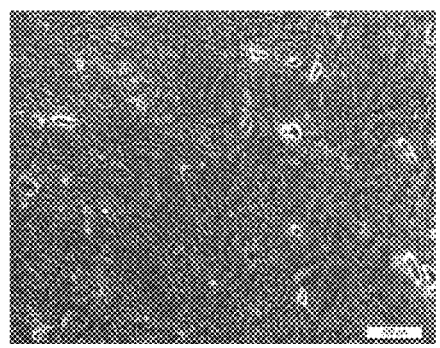
FIG. 8C shows images demonstrating differentiation of umbilical cord tissue into osteogenic lineages in accordance with another aspect of the present disclosure.
Figure 8D:
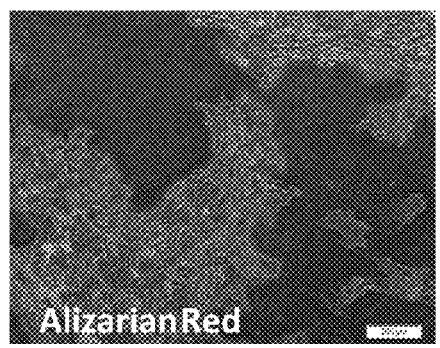
FIG. 8D shows images demonstrating differentiation of umbilical cord tissue into osteogenic lineages in accordance with another aspect of the present disclosure.

For osteogenic differentiation of SL cells, one non-limiting technique cultures such cells in the presence of StemPro Osteogenic Differentiation media (Life Technologies). As is shown in FIG. 8A, for example, differentiated SL cells are positive for the osteogenic markers OP, ON, and AP (lane 1). For osteogenic differentiation, confirmation was determined by Alizarin red staining and osteocalcin immunocytochemistry. FIG. 8B shows an image of DAPI stained cells showing the presence of osteocalcin. FIG. 8C shows unstained cells and FIG. 8D shows an image of cells stained with alizarin red demonstrating the presence of calcific deposition in the cells.

Figure 9A:
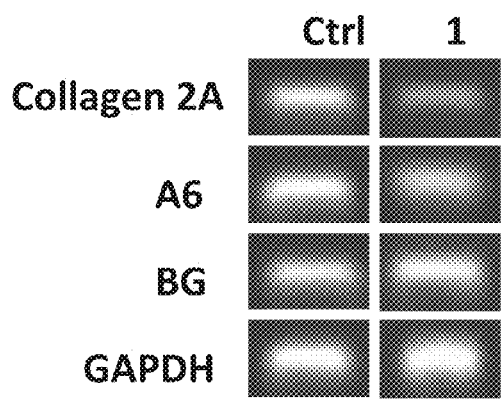
FIG. 9A shows an image demonstrating differentiation of umbilical cord tissue into Chondrogenic lineages in accordance with another aspect of the present disclosure.
Figure 9B:
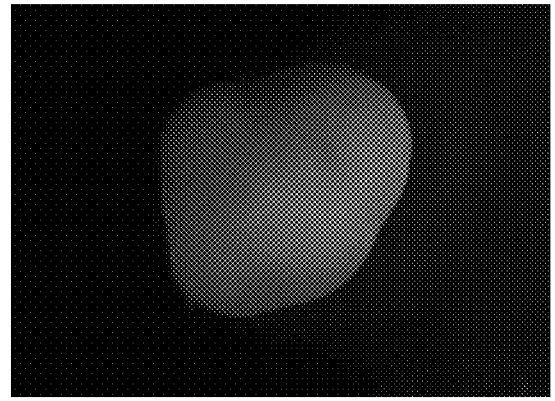
FIG. 9B shows an image demonstrating differentiation of umbilical cord tissue into Chondrogenic lineages in accordance with another aspect of the present disclosure.

For chondrogenic differentiation of SL cells, one non-limiting technique cultures SL cells in the presence of StemPro Chondrogenic Differentiations media (Life Technologies). As is shown in FIG. 9A, differentiated SL cells are positive for chondrogenic markers Collagen 2A, A6, and BG (lane 1). For chondrogenic differentiation, confirmation was determined by Von Kossa staining. FIG. 9B shows Alcian blue staining of a chondrocyte pellet.

For cardiogenic differentiation of SL cells, one non-limiting technique cultures cells in the presence of DMEM low glucose without phenol red, 1× glutamine, 1× NEAA and 10% PRP lysate or platelet lysate with 5-10 µM 5-AZA-2'-deoxycytidine.

Figure 10A:
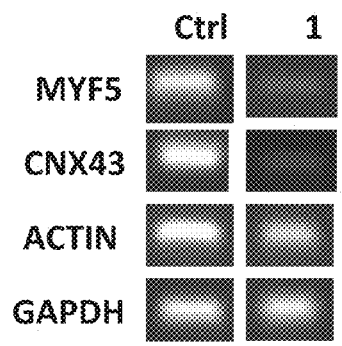
FIG. 10A shows an image demonstrating differentiation of umbilical cord tissue into cardiogenic lineages in accordance with another aspect of the present disclosure.
Figure 10B:
FIG. 10B shows an image demonstrating differentiation of umbilical cord tissue into cardiogenic lineages in accordance with another aspect of the present disclosure.
Figure 10C:
FIG. 10C shows an image demonstrating differentiation of umbilical cord tissue into cardiogenic lineages in accordance with another aspect of the present disclosure.
Figure 10D:
FIG. 10D shows an image demonstrating differentiation of umbilical cord tissue into cardiogenic lineages in accordance with another aspect of the present disclosure.

As is shown in FIG. 10A, differentiated SL cells are positive for the cardiogenic markers MYF5, CNX43, and ACTIN (lane 1). For cardiogenic differentiation, confirmation was determined by staining for ANP, tropomyosin, and troponin 1. FIG. 10B shows an image of DAPI stained cells demonstrating the presence of Troponin 1. FIG. 10C shows an image of DAPI stained cells demonstrating the presence of tropomyosin. FIG. 10D shows a merged image of the images from FIGS. 10B and 10C.

In yet another aspect, a method of treating a medical condition is provided. In some embodiments, such a method can include introducing cells described herein into an individual having the medical condition. Cells can be delivered at various doses such as, without limitation, from about 500,000 to about 1,000,000,000 cells per dose. In some aspects, the cell dosage range can be calculated based on the subject's weight. In certain aspects, the cell range is calculated based on the therapeutic use or target tissue or method of delivery. Non-limiting examples of medical conditions can include COPD, diabetes, ischemia, osteoarthritis, orthopedic damage, liver damage, chronic refractory angina, congestive heart failure, asthma, emphysema, wounds, erectile dysfunction, spinal cord injuries, herniated disks, acute radiation syndrome, neurological disorders, graft vs. host disease, autoimmune disorders, renal failure, autoimmune disorders, and the like, including combinations thereof. The treatment can include introducing cells into a region of the subject where the medical condition can be treated. The cells can be delivered intramuscularly, intravenously, intraarterially, subcutaneously, surgically, intrathecally, intraperitoneally, intranasally, orally, topically, rectally, vaginally, via aspiration, and the like, including combinations thereof. Additionally, in one aspect, undifferentiated SL cells can be delivered to the subject to treat the medical condition. In another aspect, differentiated SL cells can be delivered to the subject to treat the medical condition.

Stem cells can also be delivered into an individual according to retrograde or antegrade delivery. As an example, cells can be introduced into an organ of an individual via retrograde delivery of the cells into the organ. Non-limiting examples of such organs can include the heart, the liver, a kidney, the brain, pancreas, and the like.

Additionally, in some aspects SL cells can be lysed and the lysate used for treatment. In other aspects, supernatant from the culture process can be used for treatment. One example of such a supernatant treatment includes the delivery of exosomes. Exosomes can be delivered into the individual via aerosolized delivery, IV delivery, or any other effective delivery technique. Exosomes can also be used to treat individuals with open wounds, ulcers, burns, and the like.

In a further aspect, a method of treating COPD is provided. Such a method can include administering a COPD effective active agent intravenously to a patient to deliver the COPD effective active agent to a lower half of the patient's lung, and also administering the COPD effective active agent in an aerosolized form to the patient via ventilation to deliver the COPD effective active agent to an upper half of the patient's lung. In some embodiments, the administration can be concomitant. In other aspects, the administration can be sequential. In some aspects, the COPD effective agent delivered intravenously can be different from the COPD effective agent delivered in aerosol form, while in other aspects the same COPD effective agent can be utilized in both administrations. In some cases it can be beneficial for the patient to be in a sitting position during delivery of the COPD effective active agent. In one aspect, the COPD effective active agent includes stem cells. In another aspect, the stem cells include the cells described herein. In another aspect, the active agent can be a pharmaceutical agent, or a biologic agent. Other non-limiting examples of COPD effective active agents can include exosomes, cell lysates, protein extracts, protein extracts derived from cell culture, and the like.

A variety of conditions can be utilized to aerosolize cells. In one aspect, for example, cells can be suspended in 1-5 mls of saline and aerosolized at a pressure of 3-100 psi for 1-15 minutes, or until the cells begin to rupture and/or die.

Any form of aerosolizer can be utilized to deliver stem cells to the lungs provided the stem cells can be delivered substantially without damage. In some cases, it can be beneficial to aerosol stem cells via an aerosolizer capable of aerosolizing particles to in larger sizes. For example, in one aspect, an aerosolizer can be used that aerosolizes to a particle size of from about 2 microns to about 50 microns. In another aspect, an aerosolizer can be used that aerosolizes to a particle size of from about 4 microns to about 30 microns. In yet another aspect, an aerosolizer can be used that aerosolizes to a particle size of from about 6 microns to about 20 microns. In yet another aspect, an aerosolizer can be used that aerosolizes to a particle size of from about 6 microns to about 200 microns.

In another example, the present techniques can be utilized in the treatment of acute radiation syndrome. Acute radiation syndrome can be challenging to treat, with survival being dependent on the dose of radiation and the subsequent clinical care to mediate lethal infections, including providing support for resident stem cell expansion. Traditional techniques utilize growth factor treatment or hematopoteitic stem cell transplantation. The stem cells according to aspects of the present disclosure can be used under allogeneic transplant models with no HLA matching needed between donor and host. The cells have been shown to be hypoimmunogenic and not recognized by the immune system, even following multiple injections. These stem cells secrete several bioactive molecules, such as hematopoietic growth factors including IL6, IL11, LIF SCF and Fly3 ligand and immunomodulatory molecules such as TGFB1, prostaglandin E2, indoleamine 2,3-dioxygenase.

Such cultured cells facilitate a protective mechanism combating the inflammatory cascade in addition to supporting detoxification after radiation exposure. In addition, these cells release trophic factors and HSC-niche modulating activity to rescue endogenous hematopoiesis and activity. This data suggest that these cells serve as a fast and effective treatment in a first-line of defense to combat radiation-induced hematopoietic failure. In addition these cells may be used to treat severe or steroid resistant graft vs. host disease.

EXAMPLES

Example 1

Composition for Culturing Cells or Stem Cell from Umbilical Cord for Clinical Use Media Composition-1
DMEM-Low Glucose—Phenol Free
1× Glutamine
1× NEAA
10% PRP Lysate or platelet lysate
1000 units of heparin
Media Composition-2
DMEM-Low Glucose—Phenol Free
1× Glutamine
1× NEAA
Lyophilized 10% PRP Lysate or platelet lysate Tablet
1000 units of heparin
Media Composition-3
DMEM-Low Glucose—Phenol Free
1× Glutamine
1× NEAA
10% PRP Lysate or platelet lysate
ACD Example 2

Culturing Cells or Stem Cell from Umbilical Cord for Clinical Use

Umbilical cord tissue is obtained and maternal blood is tested for infectious disease prior to derivation of cell and stem cell populations. A 1 cm piece of cord is washed 10 times in a solution of DPBS containing 10% PRP-Lysate or platelet lysate. The umbilical cord is then opened longitudinally to expose the interior of the umbilical cord. All tissue is removed that can give rise to endothelial cells. The umbilical cord is then place directly into a cell culture dish containing Media Composition-1 with the interior of the umbilical cord in contact with the plastic and cultured in either normoxic or hypoxic culture environments.

On the third day the media is replaced with fresh Media Composition-1 and cultured until day seven when the explants are removed for primary cell expansion. The cells are fed every other day until approximately 500,000-1,000,000 cells can be harvested and further expanded. It is noted that the media used for subsequent examples is Media Composition-1 unless specifically noted otherwise.

Example 3

Enzymatic Passage of Cells or Stem Cell from Umbilical Cord for Clinical Use

TrypLE can be used for subculturing the cells. The media is removed from the flask of Example 2 and the cells are washed three times with DPBS. TrypLE is then added and the cells are transferred to the incubator at 37 C for 3-5 minutes. The enzymatic reaction is stopped by the addition of equal volume of culture/expansion media. The cells are then centrifuged 400×g for 5 minutes at room temperature. The supernatant is removed and the cells are washed 3 times if they will be further subcultured or 10 times if they will be used therapeutically.

Example 4

Non-Enzymatic Passage of Cells or Stem Cell from Umbilical Cord for Clinical Use For a non-enzymatic approach, a semi-solid gel can be used to remove the cells from the tissue culture flask. The cells are cultured in normal culture/expansion media. One day prior to subculture, freshly prepared DMEM-Low Glucose—Phenol Free, 1× Glutamine, 1× NEAA, 10% PRP Lysate or platelet lysate, ACD semi-solid media is added to the cells. The cells are cultured overnight under either a normoxic or hypoxic environment. The following day a semi-solid gel is formed over the cells. To remove the cells from the dish, the side of the dish is tapped until the semi-solid gel is dislodged from the bottom. This semi-solid layer can then be removed, and the cells will be located within the semi-solid gel. If further subculture is required the semi-solid gel is transferred to additional cell culture flasks or bags for further expansion. If the cells are not to be further expanded the semi-solid layer containing the cells can be directly applied therapeutically.

Example 5

Therapeutic Use of Cells or Stem Cells from Umbilical Cord for Treating Critical Limb Ischemia Patients qualified for inclusion if they had chronic, critical limb ischemia including rest pain (Rutherford class 4) or mild-to-moderate tissue loss (Rutherford 5) and were not candidates for surgical or endovascular revascularization. Hemodynamic parameters included one of the following: ankle pressure<50 mmHg or ABI<0.4; toe pressure<40 mmHg or TBI<0.4; or TcPO2<20 mmHg on room air.

Exclusion criteria included extensive necrosis of the index limb making amputation inevitable (Rutherford class 6); uncorrected iliac artery occlusion ipsilateral to index limb; lack of Doppler signal in the index limb (ABI=0); serum creatinine≥2.0 mg/dL; active infection requiring antibiotics; active malignancy; or any hematologic disorder that prevented bone marrow harvesting.

All patients were ≥18 years of age and able to provide informed consent. All enrolled patients underwent pre-operative cancer screening and ophthalmologic examinations for proliferative retinopathy.

Cells were produced as described in Examples 1-4. The vascular surgeon made 40 intramuscular injections of 1 mL aliquots of cells or stem cells derived from umbilical cord into previously identified locations along the ischemic limb using ultrasound guidance. Procedures were carried out under local anesthesia and conscious sedation.

Figure 11A:
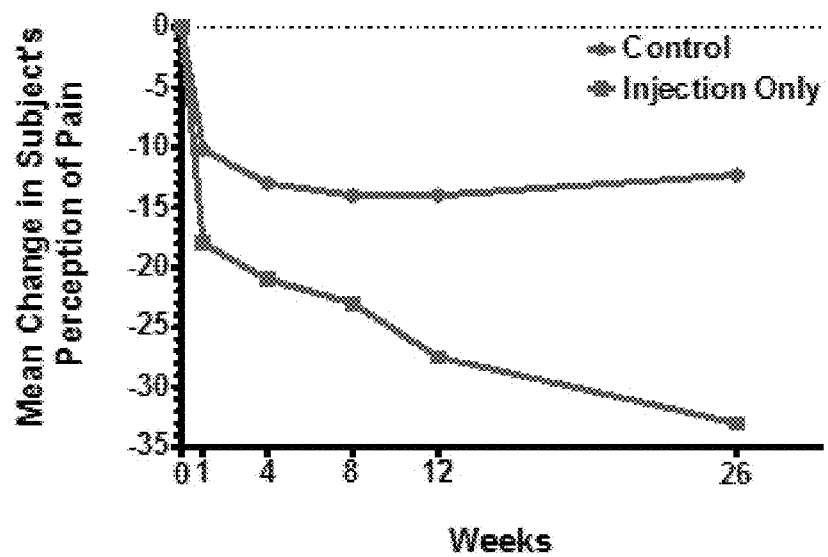
FIG. 11A shows data relating to chronic limb ischemia and pain perception over time in accordance with another aspect of the present disclosure.
Figure 11B:
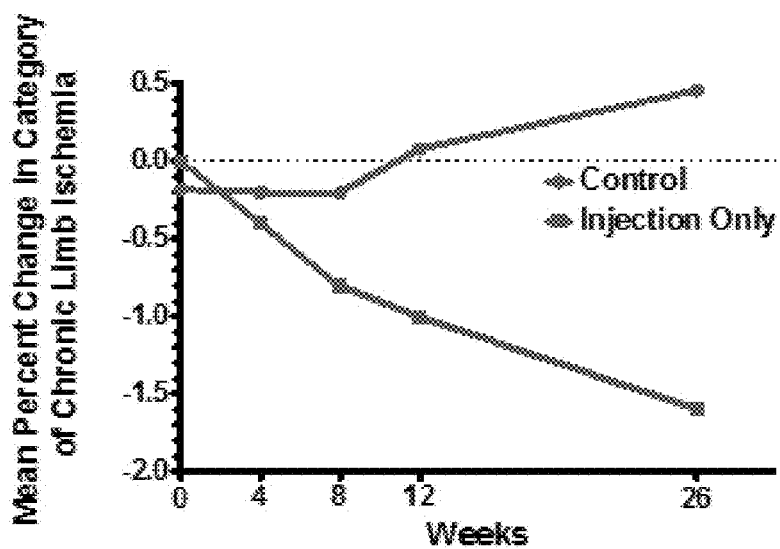
FIG. 11B shows data relating to chronic limb ischemia and pain perception over time in accordance with another aspect of the present disclosure.

Patients were evaluated at 1, 4, 8, 12 and 26 weeks post-procedure. Clinical outcomes included amputation status, Rutherford classification of limb ischemia, and pain as determined by Visual Analog Scale (VAS). Major amputations were defined as those occurring above the ankle Hemodynamic outcome was evaluated by Ankle Brachial Index (ABI). Laboratory monitoring of hematology and blood chemistries was also performed. Ophthalmologic retinal examination was performed at baseline and 12 weeks in diabetics to evaluate for proliferative retinopathy. Results are shown in FIGS. 11A and 11B. Injection only represents the delivery of stem cells, while the control was a saline solution lacking the stem cells.

Example 6

Therapeutic Use of Cells or Stem Cells from Umbilical Cord for Treating Chronic Refractory Angina and/or Congestive Heart Failure Patients with Canadian Cardiovascular Society (CCS) class III-IV angina despite maximal medical or surgical therapy who were ineligible for further percutaneous or surgical revascularization (based on coronary anatomy) and who had evidence for reversible ischemia on an exercise single photon emission computed tomography (SPECT) were enrolled.

Figure 12:
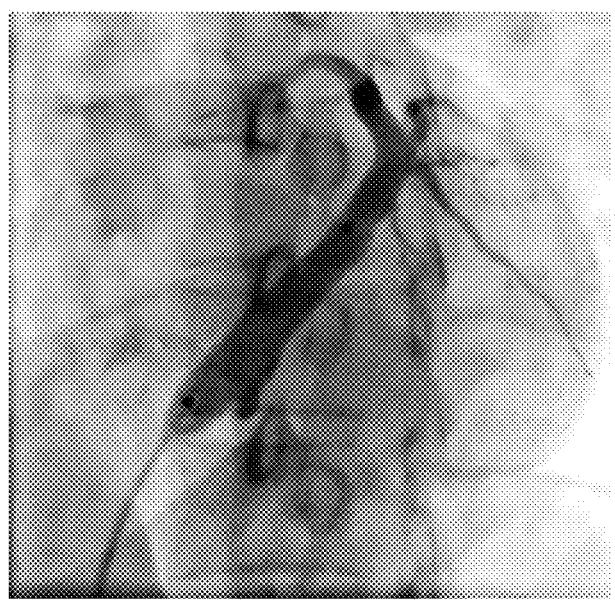
FIG. 12 shows an image of an angiogram demonstrating delivery of cells into the heart in accordance with another aspect of the present disclosure.
Figure 13A:
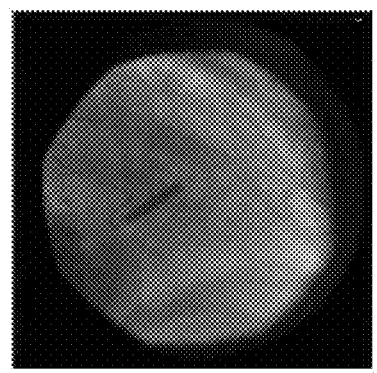
FIG. 13A shows an image in a series of images of an angiogram demonstrating delivery of cells into the heart in accordance with another aspect of the present disclosure.
Figure 13B:
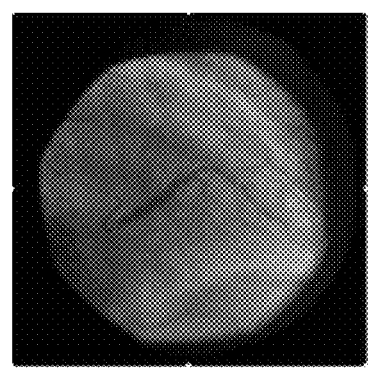
FIG. 13B shows an image in a series of images of an angiogram demonstrating delivery of cells into the heart in accordance with another aspect of the present disclosure.
Figure 13C:
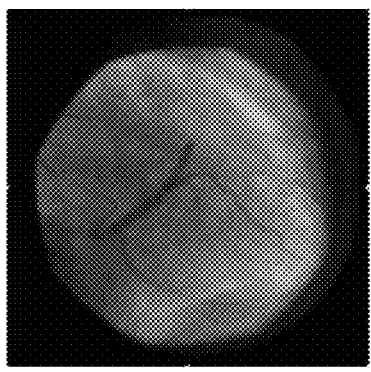
FIG. 13C shows an image in a series of images of an angiogram demonstrating delivery of cells into the heart in accordance with another aspect of the present disclosure.
Figure 13D:
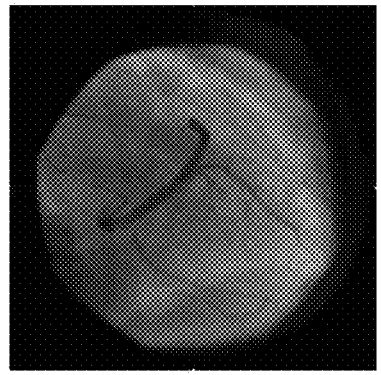
FIG. 13D shows an image in a series of images of an angiogram demonstrating delivery of cells into the heart in accordance with another aspect of the present disclosure.

Cells were produced as described in Examples 1-4. The femoral vein was cannulated with a 7 French sheath, a 6 French catheter was placed in the coronary sinus and a 0.035 mm hydrophilic guide wire was placed in the interventricular or lateral vein followed by placement of a peripheral balloon into the mid portion of the coronary sinus to allow nonselective delivery of cells. (Cook Medical, Indiana, USA). The balloon was inflated at very low pressure (1 to 2 atm) for 10 minutes producing stagnation of the flow. 50 mls of cells (50,000,000-400,000,000) were injected manually through the balloon at a rate of 10 mls per minute. The average total procedure time for cell delivery was 30 minutes. FIG. 12 shows an angiogram demonstrating delivery of cells into the heart using a retrograde technique.

The baseline screening assessment of patients included clinical evaluation, electrocardiogram (ECG), laboratory evaluation (complete blood count, blood chemistry, erythrocyte sedimentation rate, creatine kinase, and troponin T serum levels). Patients kept a record of daily angina frequency for three weeks, and the severity of angina was graded according to the CCS class at baseline, 3, 12, and 24 months. Within two weeks prior to cell therapy, exercise capacity was evaluated using bicycle ergometry in conjunction with SPECT imaging to assess myocardial ischemia and left ventricular (LV) function.

Example 7

Heart Failure Safety Study

Ten patients, 5 ischemic and 5 non-ischemic, received retrograde delivery of cells to the heart as described in Example 6. FIGS. 13A-D shows time lapse images of such a retrograde delivery. The baseline screening assessment of patients included clinical evaluation, electrocardiogram (ECG), laboratory evaluation (complete blood count, blood chemistry, erythrocyte sedimentation rate, creatine kinase, and troponin T serum levels). Patients were given follow up assessments at 1, 3, 6, and 12 months. Tables 1 and 2 show results over time for ischemic and non-ischemic patients.

TABLE 1

| Ischemic | Baseline | 1 month | 3 month |
|---|---|---|---|
| Troponin | 0.03 | 0.02 | 0.02 |
| BNP | 543 | 320 | 178 |
| EF % | 26 | 33 | 38 |
| 6 m.w. | 255 | 260 | 344 |
| VO$_2$ Max | 14 | 15 | 17 |
| AE/SAE | 0/0 | 1/0 | 1/0 |

TABLE 2

| Non-Ischemic | Baseline | 1 month | 3 month |
|---|---|---|---|
| Troponin | 0.03 | 0.03 | 0.02 |
| BNP | 655 | 389 | 156 |
| EF % | 22 | 34 | 39 |
| 6 m.w. | 227 | 235 | 312 |
| VO$_2$ Max | 13 | 15 | 19 |
| AE/SAE | 0/0 | 0/0 | 1/0 |

Example 8

Therapeutic Use of Cells or Stem Cells from Umbilical Cord for Diabetes

Cells are produced as described in Examples 1-45. Therapeutic doses can be 50,000,000-400,000,000. The cells are delivered thru arterial access into the celiac and or SMA artery, thereby delivering cells into the head and/or tail of the pancreas via infusion technique.

Example 9

Therapeutic Use of Cells or Stem Cells from Umbilical Cord for Treating COPD/Asthma/Emphysema The following inclusion criteria were used for subjects in this study. Individuals were included having:
  moderate or severe COPD with a post-bronchodilator FEV1/FVC ratio <0.7
  subject must have a post-bronchodilator FEV1% predicted value >30%
  current or ex-smoker, with a cigarette smoking history of >20 pack-years
Subjects exhibiting one or more of the following were excluded from the study:
  diagnosed with asthma or other clinically relevant lung disease other than COPD (e.g. restrictive lung diseases, sarcoidosis, tuberculosis, idiopathic pulmonary fibrosis, bronchiectasis, or lung cancer)
  diagnosed with α1-Antitrypsin deficiency
  body mass greater than 150 kg or less than 40 kg
  subject has an active infection
  subject has had a significant exacerbation of COPD or has required mechanical ventilation within 4 weeks of screening uncontrolled heart failure, atrial fibrillation cardiopulmonary rehabilitation initiated within 3 months of screening subject has evidence of active malignancy, or prior history of active malignancy that has not been in remission for at least 5 years subject has a life expectancy of <6 months Cells are produced as described in Examples 1-4. Therapeutic doses can be 50,000,000-400,000,000 cells. While a subject is sitting upright the cells are administered simultaneously thru an aerosolized delivery which will remain top half of the lung due to normal physiologic ventilation perfusion and is given intravenous which is delivered to the lower half of the lung, due to the natural ventilation perfusion for a person sitting upright. This combined technique is used due to the fact that either one performed alone does not deliver sufficient biologic to the entire lung volume.

20 test subjects were divided into 4 groups and received the following:

5 subjects in Group 1 were given placebo—saline injection 5 subjects in Group 2 were given IV delivery—200M cells 5 subjects in Group 3 were given inhaled delivery—200M cells 5 subjects in Group 4 were given IV and inhaled delivery—100M/100M cells Results obtained from these groups treated with no cells, IV only, inhaled only and both IV and inhaled are shown in Table 3.

Regarding aerosolization, cells were prepared as described, suspended in 1-5 mls of saline and aerosolized at a pressure of 30 psi for 8-10 minutes

TABLE 3

|  | Placebo Group 1 | IV Group 2 | Inhaled Group 3 | IV and Inhaled Group 4 |
| --- | --- | --- | --- | --- |
| FEV1/FVC pre | 0.55 ± 0.15 | 0.49 ± 0.08 | 0.51 ± 0.10 | 0.47 ± 0.07 |
| FEV1/FVC post | 0.52 ± 0.13 | 0.53 ± 0.12 | 0.57 ± 0.11 | 0.66 ± 0.05 |
| O$_2$L/min pre | 3.0 ± 1.0 | 2.8 ± 1.2 | 3.2 ± 1.0 | 2.8 ± 1.2 |
| O$_2$L/min post | 3.2 ± 1.2 | 2.4 ± 1.4 | 2.5 ± 1.2 | 2.0 ± 1.0 |
| MAP/CE | 2 | 0 | 0 | 0 |

Example 10

Therapeutic Use of Cells or Stem Cells from Umbilical Cord for Treating Wound Healing Cells are produced as described in Examples 1-4. Therapeutic doses can be 50,000,000-400,000,000 cells in this example. Cells are delivered to the wound via injection and/or aerosolized in a PL-carrier with addition of liquid calcium and thrombin.

Example 11

Figures 14A, 14B:
FIG. 14A shows an image of a series of images of the knee of an 80 year old female prior to and following the delivery of stem cells into the intraarticular space in accordance with another aspect of the present disclosure.
FIG. 14B shows an image of a series of images of the knee of an 80 year old female prior to and following the delivery of stem cells into the intraarticular space in accordance with another aspect of the present disclosure.
Figures 14C, 14D:
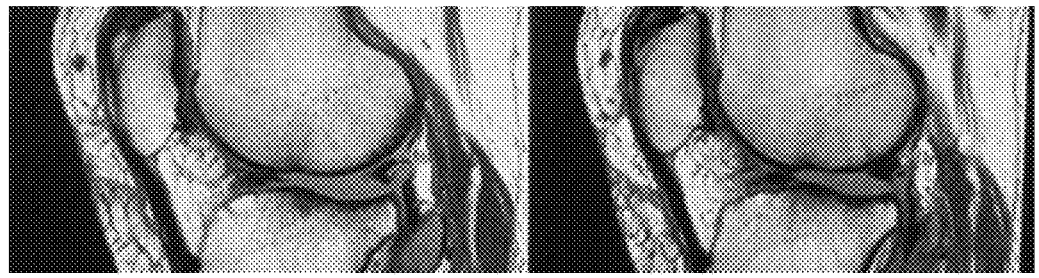
FIG. 14C shows an image of a series of images of the knee of an 80 year old female prior to and following the delivery of stem cells into the intraarticular space in accordance with another aspect of the present disclosure.
FIG. 14D shows an image of a series of images of the knee of an 80 year old female prior to and following the delivery of stem cells into the intraarticular space in accordance with another aspect of the present disclosure.

Therapeutic Use of Cells or Stem Cells from Umbilical Cord for Orthopedic Applications Cells are produced as described in Examples 1-4. Therapeutic doses can be 50,000,000-400,000,000 cells in this example. Under ultrasound guidance the cells are directly injected into the intraarticular space/joint with or without a micro fracture technique. They cells may also be delivered with PRPL or PL carrier in addition to liquid calcium/thrombin. As one example, FIGS. 14A and 14B show images of the knee of an 80 year old female prior to the delivery procedure. FIGS. 14C and 14D show images of the same knee from the same 80 year old female 3 months post-transplant. It is noted that more intraarticular space is observed in the patient in the post-transplant images.

Example 12

Figure 15A:
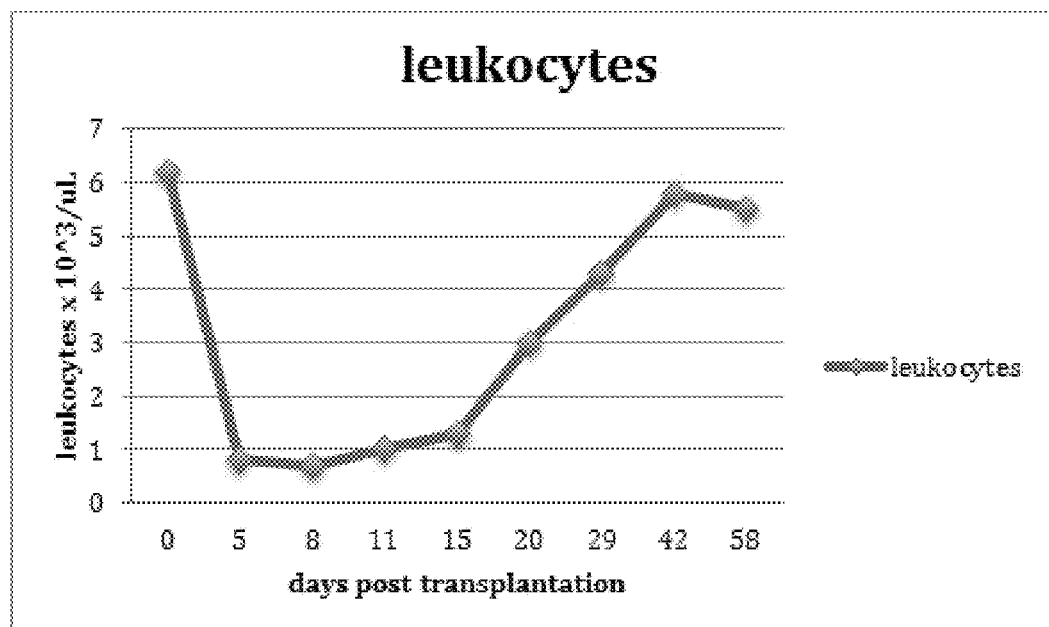
FIG. 15A shows data relating to acute radiation syndrome in accordance with another aspect of the present disclosure.
Figure 15B:
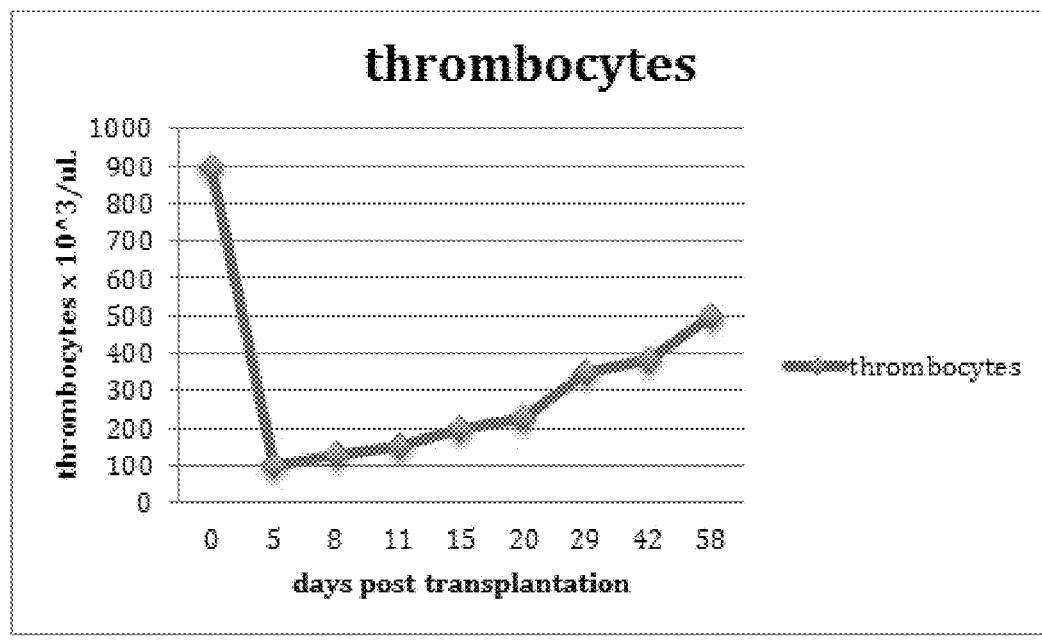
FIG. 15B shows data relating to acute radiation syndrome in accordance with another aspect of the present disclosure.

Therapeutic Use of Cells or Stem Cells from Umbilical Cord for Acute Radiation Syndrome Applications in Mice Female C57BL/6J mice were used as the recipient population. Umbilical cord stem cells were isolated as previously described but isolated in this case from mice. The female C57BL/6J mice received TBI using a Cs-137 radiation source. Lethal irradiation was performed using 9.5 Gy. Within 8 hours post irradiation mice received transplants intravenously. Evaluation of peripheral blood counts of animals treated with stem cells revealed similar leukocyte and thrombocyte recovery as observed in recipients treated with HSCs. (See FIGS. 15A-B) Seven months post transplantation recipients were hematologically well with a normal distribution of peripheral blood cell populations. (See Table 4).

TABLE 4

| Peripheral blood cell population in transplanted mice | | | |
| --- | --- | --- | --- |
| lymphocytes | neutrophils | monocytes | eosinophils |
| 72% +/− 3 | 21% +/− 3 | 5% +/− 2 | 2% +/− 1 |

Example 13

Figure 16:
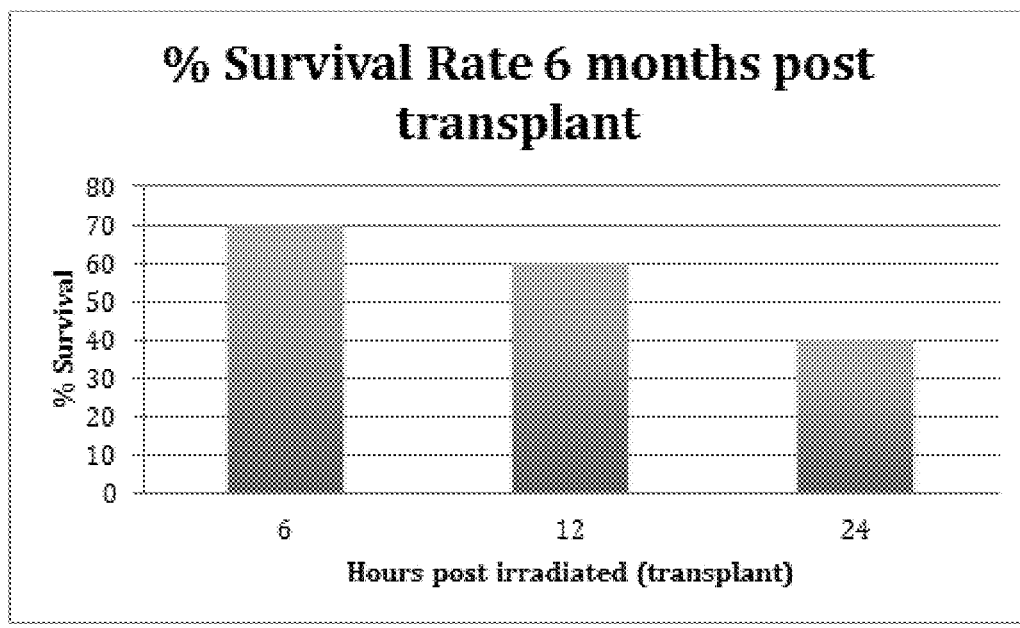
FIG. 16 shows data relating to acute radiation syndrome in accordance with another aspect of the present disclosure.

Therapeutic Use of Cells or Stem Cells from Umbilical Cord for Acute Radiation Syndrome Applications in Humans In order to determine if human derived subepithelial layer umbilical cord cells had the same effect as Example 12, the same experiment was repeated using human-derived cells as the donor material and nod/scid gamma(c) null mice as the recipient. Animals were treated as previously described and transplanted IV at 6, 12 and 24 hours post total body irradiation (TBI). 6 months post transplant all (n=30) control mice that didn't receive cells post TBI were dead. FIG. 16 shows the survival of mice receiving human cells 6, 12 and 24 hours post TBI.

Of course, it is to be understood that the above-described arrangements are only illustrative of the application of the principles of the present disclosure. Numerous modifications and alternative arrangements may be devised by those skilled in the art without departing from the spirit and scope of the present disclosure and the appended claims are intended to cover such modifications and arrangements. Thus, while the present disclosure has been described above with particularity and detail in connection with what is presently deemed to be the most practical embodiments of the disclosure, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. An isolated cell prepared by a process comprising:
    placing a subepithelial layer of a mammalian umbilical cord tissue in direct contact with a growth substrate; and
    culturing the subepithelial layer such that the isolated cell from the subepithelial layer is capable of self-renewal and culture expansion,
    wherein the isolated cell expresses at least three cell markers selected from the group consisting of CD29, CD73, CD90, CD166, SSEA4, CD9, CD44, CD146, or CD105, and
    wherein the isolated cell does not express NANOG and at least five cell markers selected from the group consisting of CD45, CD34, CD14, CD79, CD106, CD86, CD80, CD19, CD117, Stro-1, or HLA-DR.

2. The isolated cell of claim 1, wherein the isolated cell expresses CD29, CD73, CD90, CD166, SSEA4, CD9, CD44, CD146, and CD105.

3. The isolated cell of claim 1, wherein the isolated cell does not express CD45, CD34, CD14, CD79, CD106, CD86, CD80, CD19, CD117, Stro-1, and HLA-DR.

4. The isolated cell of claim 1, wherein the isolated cell is positive for SOX2.

5. The isolated cell of claim 1, wherein the isolated cell is positive for OCT4.

6. The isolated cell of claim 1, wherein the isolated cell is positive for SOX2 and OCT4.

7. The isolated cell of claim 1, wherein the wherein the isolated cell is capable of differentiation into a cell type selected from the group consisting of adipocytes, chondrocytes, osteocytes, cardiomyocytes, endothelial cells, and myocytes.

8. The isolated cell of claim 1, wherein the isolated cell produces exosomes expressing CD63, CD9, or CD63 and CD9.

9. The isolated cell of claim 1, wherein culturing comprises culturing in a culture media that is free of animal components.

10. A culture of differentiated cells derived from the isolated cell of claim 1, wherein the culture of differentiated cells includes a cell type selected from the group consisting of adipocytes, chondrocytes, osteocytes, cardiomyocytes, endothelial cells, myocytes and combinations thereof.

11. The isolated cell of claim 1 that has been differentiated into an adipocyte cell.

12. The isolated cell of claim 1 that has been differentiated into a chondrocyte cell.

13. The isolated cell of claim 1 that has been differentiated into an osteocyte cell.

14. The isolated cell of claim 1 that has been differentiated into a cardiomyocyte cell.

15. The isolated cell of claim 1 that has been expanded into a cell culture.

* * * * *

(12) INTER PARTES REVIEW CERTIFICATE (4050th)

United States Patent
Patel

(10) Number: US 9,803,176 K1
(45) Certificate Issued: Jul. 17, 2025

(54) METHODS AND COMPOSITIONS FOR THE CLINICAL DERIVATION OF AN ALLOGENIC CELL AND THERAPEUTIC USES

(71) Applicant: Amit Patel

(72) Inventor: Amit Patel

(73) Assignee: JADI CELL LLC

Trial Number:

IPR2021-01535 filed Sep. 29, 2021

Inter Partes Review Certificate for:

Patent No.: 9,803,176
Issued: Oct. 31, 2017
Appl. No.: 13/732,204
Filed: Dec. 31, 2012

The results of IPR2021-01535 are reflected in this inter partes review certificate under 35 U.S.C. 318(b).

INTER PARTES REVIEW CERTIFICATE
U.S. Patent 9,803,176 K1
Trial No. IPR2021-01535
Certificate Issued Jul. 17, 2025

AS A RESULT OF THE INTER PARTES REVIEW PROCEEDING, IT HAS BEEN DETERMINED THAT:

Claims 1-15 are found patentable.

\* \* \* \* \*